(12) United States Patent
Holyfield

(10) Patent No.: US 6,505,759 B2
(45) Date of Patent: Jan. 14, 2003

(54) FRAGRANCE DISPENSER

(76) Inventor: Louise Holyfield, 5609 Bent Trail, Dallas, TX (US) 75248

( * ) Notice: Subject to any disclaimer, the term of this patent is extended or adjusted under 35 U.S.C. 154(b) by 0 days.

(21) Appl. No.: 09/865,019

(22) Filed: May 24, 2001

(65) Prior Publication Data

US 2002/0175188 A1 Nov. 28, 2002

(51) Int. Cl.[7] .................................................. B67D 5/06
(52) U.S. Cl. .................... 222/180; 222/321.8; 222/183; 248/205.3
(58) Field of Search ................................. 222/162, 180, 222/183, 320, 321.1, 321.7, 321.8; 248/205.3, 205.4

(56) References Cited

U.S. PATENT DOCUMENTS

| | | | | |
|---|---|---|---|---|
| 2,904,223 A | * | 9/1959 | Ryan | 222/162 |
| 4,765,515 A | * | 8/1988 | Lippman | 222/162 |
| 5,082,149 A | * | 1/1992 | Cross | 222/162 |
| 5,487,489 A | * | 1/1996 | Weiss et al. | 222/162 |
| 5,598,954 A | * | 2/1997 | Salzano | 222/162 |
| 6,082,592 A | * | 7/2000 | McKenna et al. | 222/162 |
| 6,230,889 B1 | * | 5/2001 | Chen | 222/162 |
| 6,305,580 B1 | * | 10/2001 | Chen | 222/162 |

* cited by examiner

Primary Examiner—Henry C. Yuen
Assistant Examiner—Stephanie L. Willatt
(74) Attorney, Agent, or Firm—Godwin Gruber, P.C.; Arthur L. Navarro

(57) ABSTRACT

A fragrance dispenser (10) for dispensing a fragrance mist can be mounted directly on a commode, tank or other surface. The fragrance dispenser (10) includes an enclosure (11), fragrance holder (16) and mounting plate (18). The enclosure (11) includes a base (14) and cover(12) attached to the base (14) so as to form a housing around the fragrance holder (16). The mounting plate (18) is flexible and has an adhesive sheet (20) attached to one side for securing the dispenser(10) to a fixed object, such as a wall or around the seat of a commode. Pressure applied to the cover (12) activates a spray pump (46) attached to the fragrance holder (16). This action causes the spray pump (46) to compress with the assistance of a rocker arm (50) and spray a fragrance mist through a fragrance nozzle (40).

9 Claims, 5 Drawing Sheets

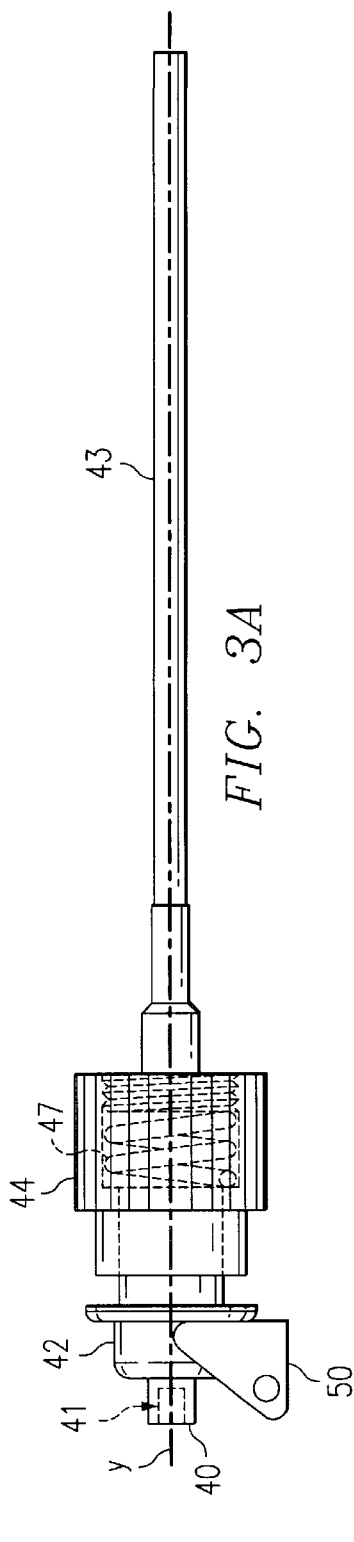
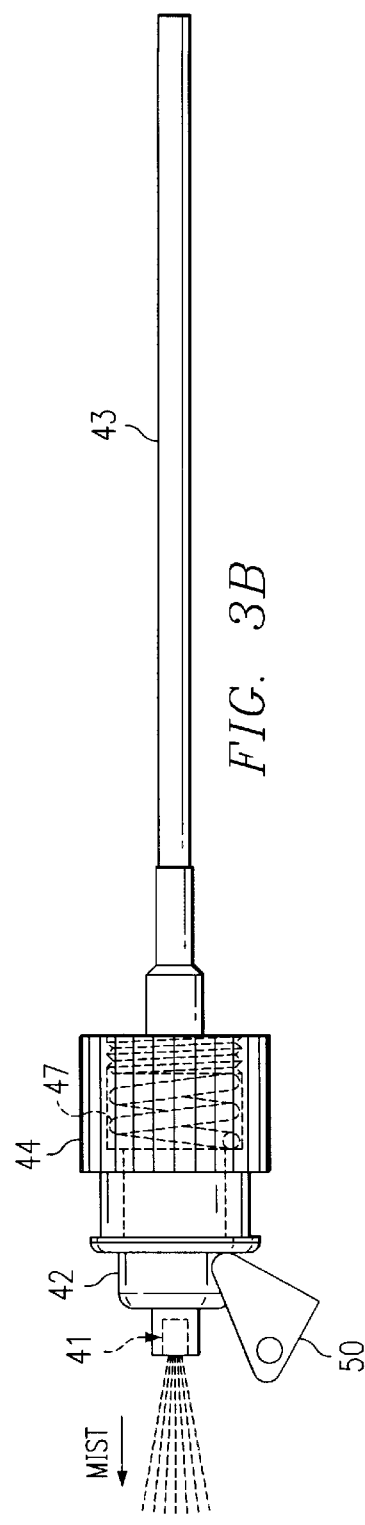
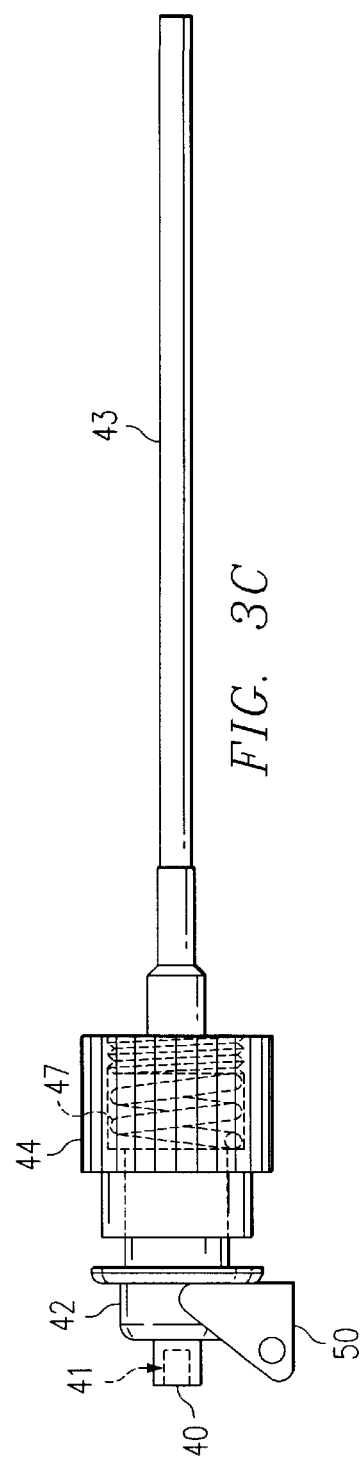

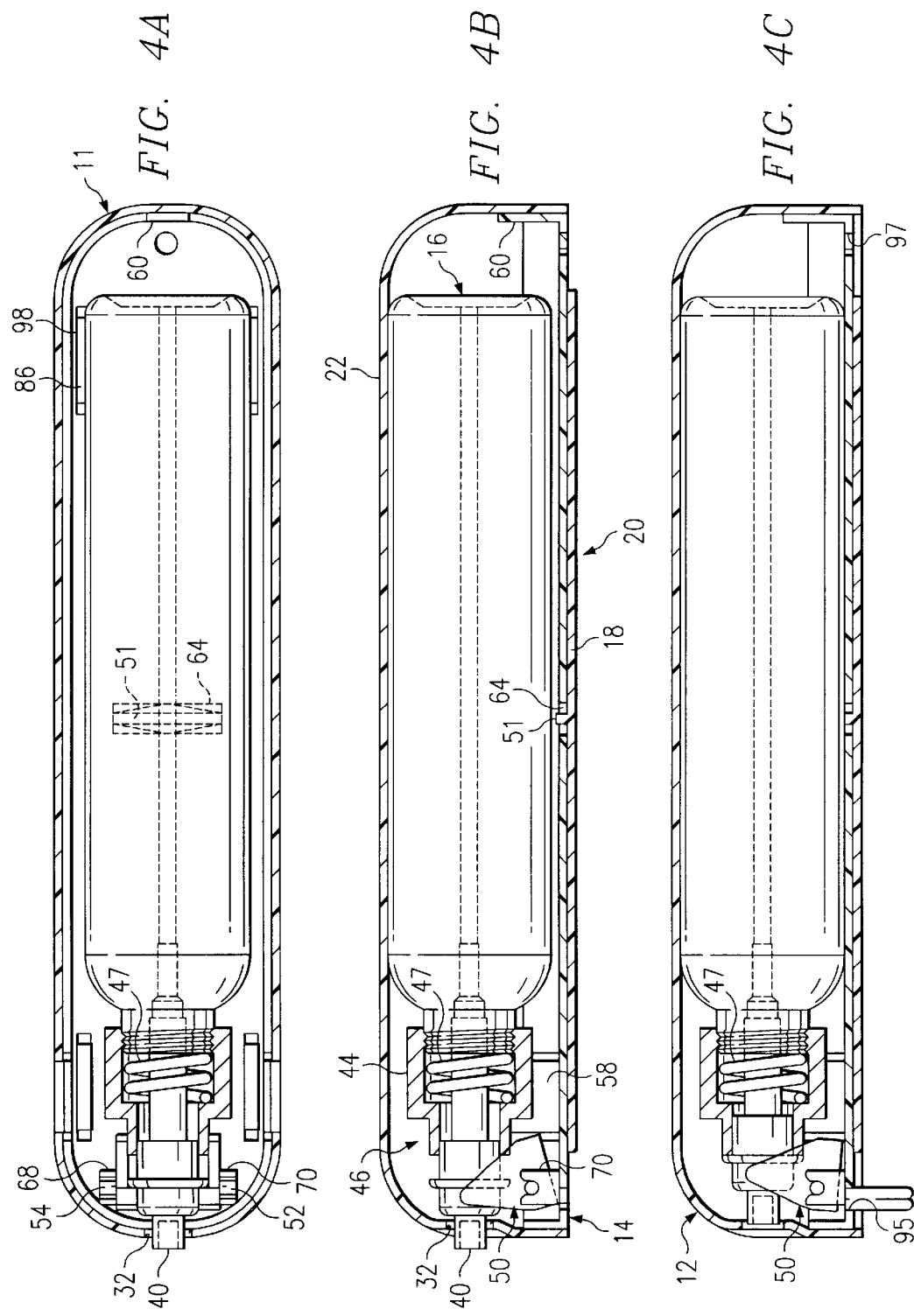

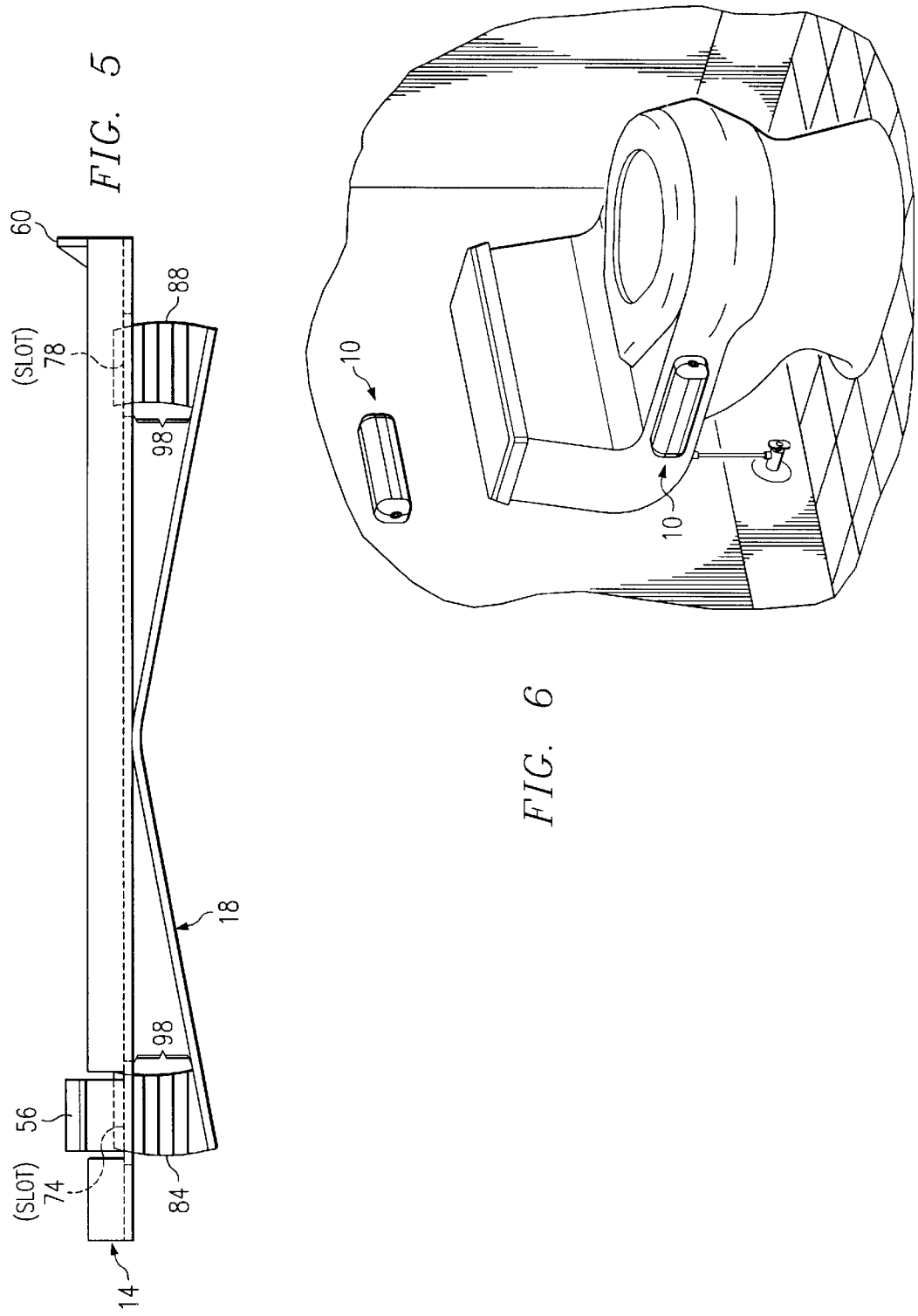

FRAGRANCE DISPENSER

TECHNICAL FIELD

The invention relates generally to a fragrance dispenser and more particularly to a fragrance dispenser mounted around the seat of a commode, tank or flat surface which is capable of dispensing an odor eliminating fragrance.

BACKGROUND OF THE INVENTIONS

For years, fragrance dispensers and deodorizers have been used to remove unpleasant bathroom odors. Traditionally, these dispensers have come in two forms: aerosol based or non-aerosol based. Unfortunately, such prior art fragrance dispensers are limited in several important aspects. First, aerosol dispensers come in an aerosol can that is not always conveniently located when needed. Secondly, aerosol cans typically have no re-fill mechanism so that once the contents inside the can are consumed the entire can itself must be disposed of and then replaced.

Non-aerosol based dispensers or deodorizers, such as scented candles, pump sprays and deodorizing tablets, also have their shortcomings. For instance, once in use these deodorizers are known to continuously deodorize an area, which means that users are seldom able to control the volume and intensity of fragrance being dispensed into a room at any specified time. Non-aerosol based dispensers are also movable and rarely have any kind of refill mechanism. A refill mechanism would minimize the cost incurred by the user of having to replace the entire deodorizer unit after the contents of the unit have been consumed. In fact, the cost incurred by users of non-aerosol based products can be substantial given the nearly uncontrollable and wasteful release of deodorizing fragrance that these non-aerosol products often produce.

Accordingly, there is a need for a conveniently located fragrance dispenser that is both stationary and re-usable. Such a dispenser would relieve the user from the burden of having to search for a deodorizer in an area such as a bathroom whenever the need to deodorize arises. Such a dispenser would also increase the user's ability to control the quantity and quality of fragrance being dispensed while simultaneously lessening the dispenser's overall replacement cost.

SUMMARY OF THE INVENTION

The present invention solves the problems of prior art fragrance dispensers and deodorizers by providing a fragrance dispenser that can be mounted on a surface, such as a bathroom wall, or directly on a bathroom commode or tank. Moreover, the present invention provides a fragrance dispenser that can be conveniently placed at or near the source of an unpleasant odor (commode or tank, for example) so as to be ready for use whenever the need to deodorize an area arises while at the same time giving the user the ability to control the quality and quantity of fragrance being dispensed into a specific area.

Accordingly, disclosed in one embodiment is a fragrance dispenser comprising an enclosure and a fragrance holder. The enclosure has an opening and comprises a base and a cover attached to the base so as to form a substantially cylindrical housing around the fragrance holder. The base includes a major surface with slots formed therein, the fragrance holder housed within the enclosure and having a nozzle that protrudes through the opening of the enclosure.

A spray pump is attached to the fragrance holder for spraying a mist of fragrance through the opening of the enclosure. Preferably, the spray pump includes a spray head and orifice cap that allows the spray pump to direct the mist along a line substantially parallel to the body of the fragrance holder. A rocker arm facilitates the action of the spray pump and is fixed within the base of the enclosure on a pair of supports which facilitate the spray action of the spray pump. During use, a user depresses the cover which forces the rocker arm to rotate within the supports and compress the spray head into the body of the enclosure such that the spray pump is activated causing the spraying of a mist outward through the opening of the enclosure. When pressure is removed from the cover of the enclosure, the rocker arm and spray head return to their original position ready for the next spray action.

In one embodiment, the fragrance dispenser includes a flexible mounting plate with grasps that are insertable in the slots of the base. Each grasp includes fins that secure the mounting plate to the base at a plurality of different positions, allowing the mounting plate to flex into a plurality of contours. An adhesive sheet is attached to the underside of the mounting plate which allows the fragrance dispenser to be attached a surface and assume the rounder contour of a commode, for example.

In one embodiment, the base of the enclosure includes holes adapted to receive a hook, screw, bracket or wall anchor for installation of the fragrance dispenser on a flat surface such as a wall. In this configuration, the mounting plate and adhesive sheet are not used.

Also disclosed is a spray mechanism for use with a liquid container such as the fragrance dispenser of the present invention. The spray mechanism comprises a spray pump and a sprayer head slidable engaged with the spray pump and having a nozzle opening. A flexible tube extends from the spray pump opposite the sprayer head and a spray cap is adapted for directing a mist through the nozzle opening in a direction substantially parallel to the body of the fragrance holder and the length of the flexible tube.

An advantage of the present invention is that the fragrance holder provides a cost effective disposable refill mechanism. The user can select from a variety of available fragrances every time a refill is installed in the fragrance dispenser.

Another advantage of the invention is a fragrance holder that can be securely mounted to a commode or tank, or flat surface, such as a wall, for eliminating odors near the source.

BRIEF DESCRIPTION OF THE DRAWINGS

The above and other advantages, as well as specific embodiments, are understood from consideration of the following detailed description taken in conjunction with the appended drawings in which:

FIGS. 3a–3c illustrate the action of the rocker arm and spray mechanism used to dispense a fragrance within the fragrance dispenser of the present invention;

FIGS. 4a–4c illustrate the rocker arm and spray mechanism of the present invention within the fragrance dispenser enclosure;

FIG. 5 shows the flexible mounting plate of the fragrance dispenser of the present invention; and FIG. 6 shows use of the fragrance dispenser of the invention both on a surface, such as on a wall, or around the seat of commode where the dispenser assumes the contour of the commode.

References and terms in the detailed description correspond to similar references in the figures unless otherwise indicated.

DETAILED DESCRIPTION OF PREFERRED EMBODIMENT

Figure 1:
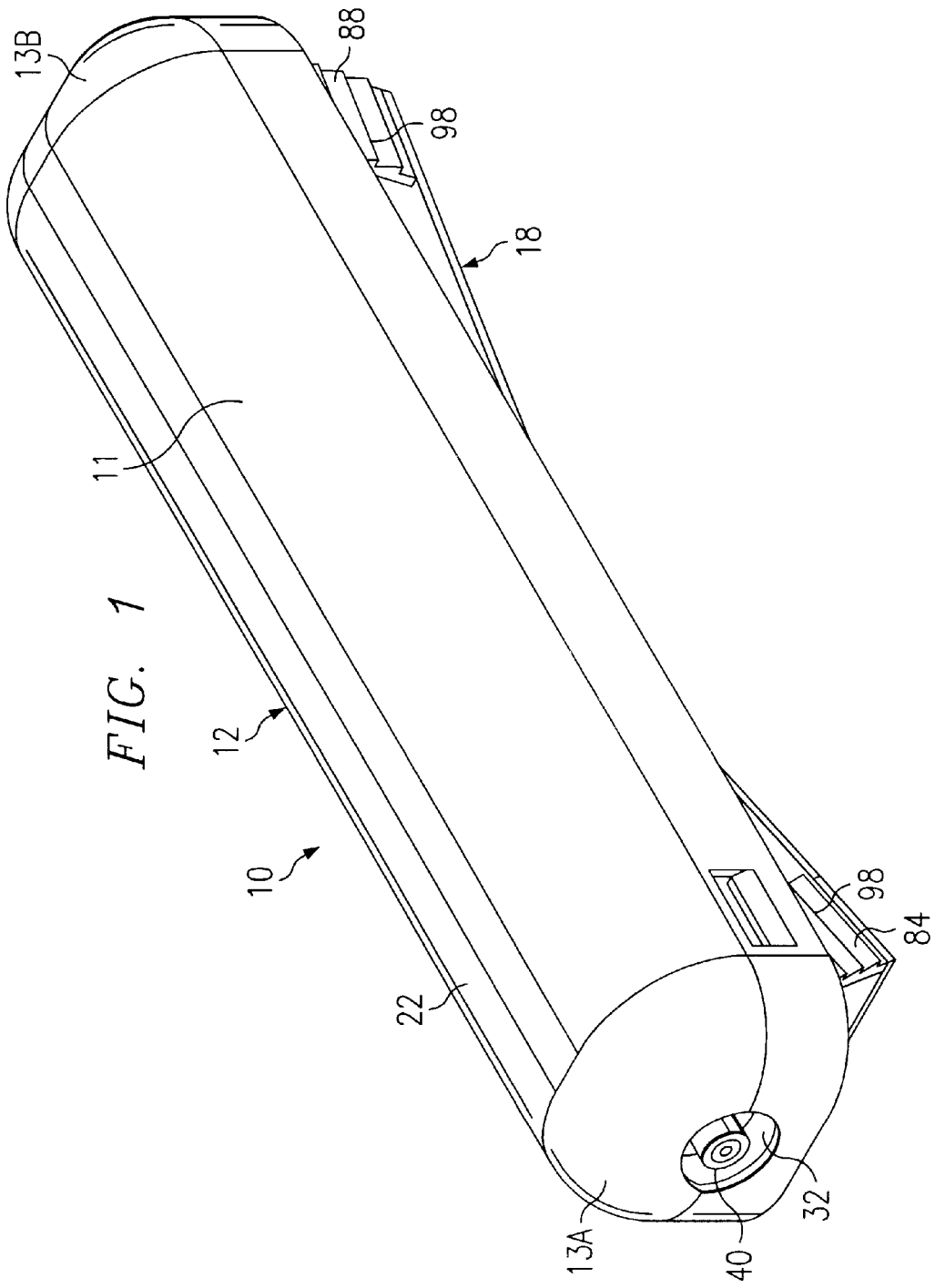
FIG. 1 illustrates a fragrance dispenser according to the present invention.
Figure 2:
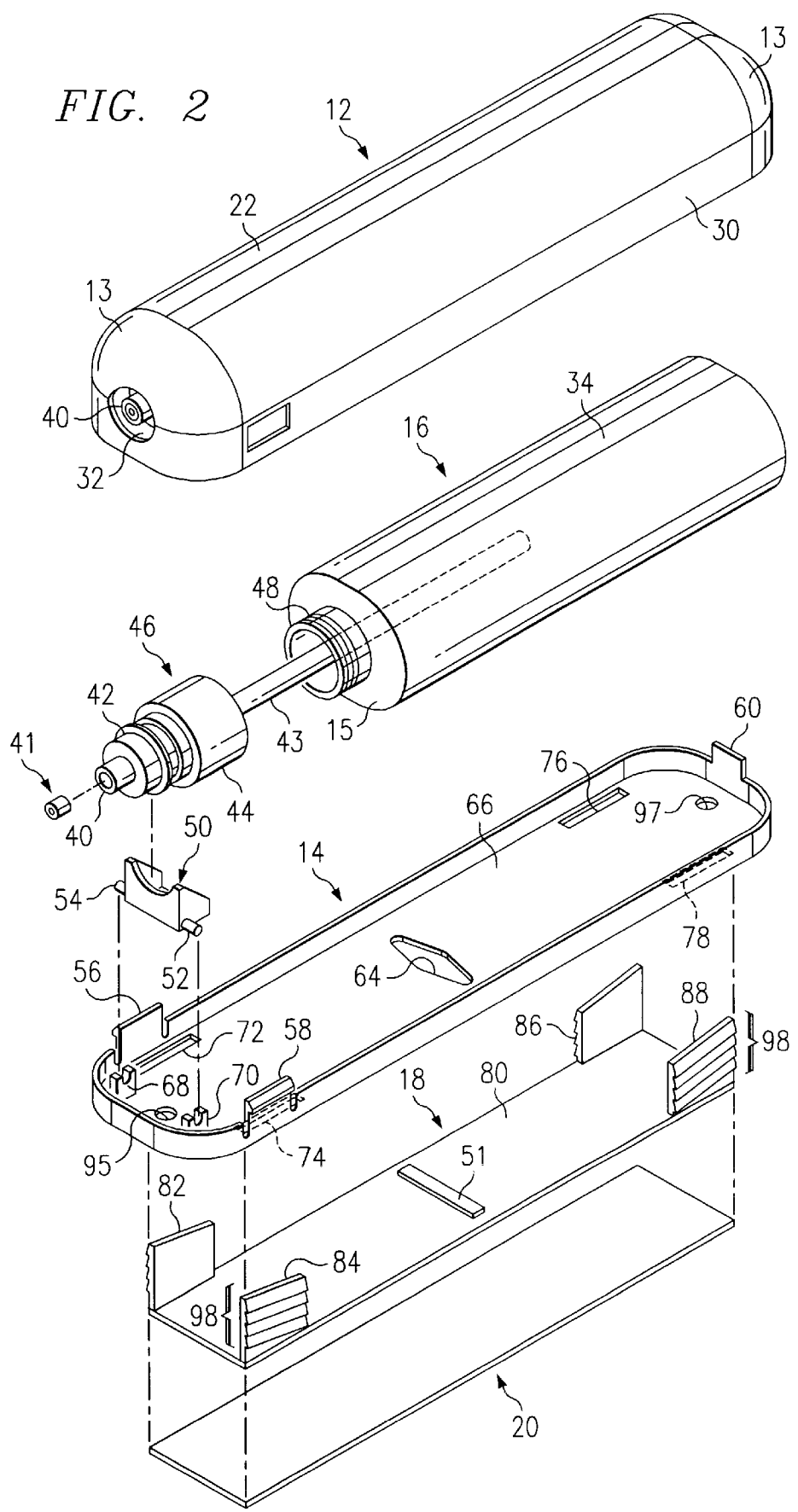
FIG. 2 is an exploded view of the fragrance dispenser of FIG. 1.

Referring to FIGS. 1 and 2, therein is illustrated a fragrance dispenser, denoted generally as 10, according to the preferred embodiment of the present invention. The fragrance dispenser 10 preferably comprises an enclosure 11 within which a fragrance holder 16 is housed. The enclosure 11 includes an opening 32 at one end 13A of the cover 12. As explained below, the cover 12 is attached to a base 14 that forms an enclosure 11 for housing the fragrance holder 16 having a spray mechanism according to the invention.

It is contemplated that the cover 12 of fragrance dispenser 10 is made of a hardened plastic material that is capable of withstanding a hand pressure applied to the cover 12 in order to operate the spray mechanism within the enclosure 11 that causes a fragrance to dispense through the nozzle 40 extending through opening 32.

With reference to FIG. 2, the fragrance dispenser 10 is shown in more detail and separated into its various parts. In particular, the fragrance dispenser 10 is shown to include a nozzle 40 which, in turn, is coupled to a spray head 42. The spray head 42 is attached to the fragrance holder 16 by, for example, the threaded members 46 and 48. As shown, the fragrance holder 16 defines a container 34 that fits within the space defined by cover 12 and base 14 when the cover 12 and base 14 are coupled to each other to form the enclosure 11. During use, the fragrance holder 16 is filled with a fragrance that can be concentrated and/or scented, allowing many uses without refill. Once emptied, the fragrance holder 16 can be re-filled or replaced with a new fragrance holder, eliminating the need to replace the enclosure 11 and thus providing a cost effective deodorizing fragrance dispensing device.

During use, the enclosure 11 can be attached to a mounting plate 18 which facilitates attachment of the fragrance dispenser 10 to a surface. The mounting plate 18 includes grasps 82, 84, 86, 88 which are insertable in corresponding slots 72, 74, 76, and 78 found on the base 14. Preferably the mounting plate 18 is used for securing the dispenser 10 to a curved surface, such as the rounded portion of a commode, tank, or counter top. As discussed below in more detail, the grasps 82, 84, 86, 88 of mounting plate 18 allow the fragrance dispenser 10 to be attached to rounded surfaces. Thus, the present invention provides a fragrance dispenser 10 capable of use in numerous environments to eliminate unwanted odors.

Still referring to FIG. 2, the details of the enclosure 11, fragrance holder 16 and flexible mounting plate 18 are better illustrated. In particular, the fragrance dispenser 10 can use an adhesive sheet 20 to attach the dispenser 10 to a surface such as a wall or directly on a commode or tank. Since the enclosure 11 includes a cover 12 attached to the base 14, a self-contained housing for the fragrance holder 16 is provided. To attach the cover 12 to the base, a plurality of latches 56, 58, 60 are provided which extend from the base 14 for securing the base 14 to the cover 12.

The base 14 includes a major surface 66 with slots 72, 74, 76, 78 formed therein through which grasps 82, 84, 86, 88 of the mounting plate 18 are inserted. Each of the grasps 82, 84, 86, 88 includes a plurality of fins 98 that assist in securing the mounting plate 18 to the base 14 about the slots 72, 74, 76, 78. The fins 98 allow the mounting plate 18 to assume different contours such that the mounting plate 18 is able to flex about a curved surface for attachment of the fragrance dispenser 10 to the rounded portion of a commode, for example. Thus, once the fins 98 are set within slots 72, 74, 76, 78, users are then able to attach the mounting plate 18 to a curved surface. The adhesive sheet 20 is provided to help secure the mounting plate 18 in place.

The base 14 includes an opening 64 on the major surface 66 through which a tab 51 of the mounting plate 18 can be inserted for securing the mounting plate 18 to the base 14 of the enclosure 10. In one embodiment, the mounting plate 18 can be slightly flexed to create an angle of entry for tab 51 through opening 64 and the base 14 can be slightly rotated to allow for parallel alignment of the base 14 and the mounting plate 18. Complete alignment of the base 14 and mounting plate 18 is achieved once each of the grasps 82, 84, 86, 88 is inserted through the corresponding slots 72, 74, 76, 78. The adhesive sheet 20 is attached to the backside of the mounting plate 18 for attaching the dispenser 10 to a surface. Alternatively, holes 95 and 97 in base 14 can be used to attach the dispenser 10 to a surface using a hook, bracket, screw, anchor or other similar device.

With reference now to FIGS. 2, 3A–3C, the spray mechanism of the fragrance dispenser 10 is shown. A rocker arm 50 is provided within the base 14 of the fragrance dispenser 10 and adapted to guide the spray head 42 of the spray pump 46 such that the spray head 42 traverses back along line Y extending through the length of the spray pump 46 and the body of fragrance holder 16. This action is shown and illustrated by FIGS. 3A and 3B. The rocker arm 50 is supported by supports 68, 72 which are integrated into the base 14 typically during manufacturing. The supports 68, 70 permit the rocker arm 50 to rotate (FIG. 3B) and compress the spray head 42 in such a way that a mist is sprayed outward from nozzle 40 and through opening 32. After spraying, the rocker arm 50 and spray head 42 return to their original position ready for another spray as shown in FIG. 3C.

A novel feature of the present invention is the manner in which the spray pump 46 is able to direct a mist out of the fragrance holder along line Y which is substantially parallel to the body of the fragrance holder 16 as well as the tube 43. Thus, according to one aspect of the invention an improved sprayer mechanism is disclosed. In particular, the spray mechanism comprises the spray pump 46 with a sprayer head 42 that is slidable engaged with the spray pump 46 and includes a nozzle opening 40. A flexible tube 43 extends from the spray pump 46 opposite the sprayer head 42 and a spray cap 41 is adapted for directing a mist through the nozzle opening 40 in a direction substantially parallel to the flexible tube 43. The direction of the mist is controlled by the cap 41 which contains the opening forming nozzle 40 (or "nozzle opening"). Thus, a spray action similar to those achieved with known spray mechanisms is obtained while maintaining a spray direction that is ideal for use in a bathroom environment. i.e., away from the user and along line Y.

With reference now to FIGS. 2, 4A–4C, therein are shown cross sections of the spray mechanism of the present invention placed inside the enclosure 11 of the fragrance dispenser 10. In particular, the layout of the fragrance holder 16 within the space of the enclosure 11 is shown. The rocker arm 50 is coupled to the inside of the base 14 within supports 68, 70. Specifically, the rocker arm 50 has pivots 52 and 54 extending therefrom which are cradled in supports 68 and 70, respectively, mounted inside the base 14. Once in position, the rocker arm 50 makes contact with a spray pump 46 at the spray head 42, such that when pressure is applied to cover 12 the spray pump 46 compresses inward into the body of the enclosure 11, thereby facilitating the spray of a fragrance from the fragrance holder 16.

Thus, the rocker arm 50 rotates within the enclosure 11 (formed by cover 12 and base 14) and causes the spray pump 46 to spray a fragrance contained within the fragrance holder 16 through flexible tube 43. Once the fragrance reaches the spray pump 46, the fragrance exits through spray nozzle 40 in the form of a fragrance mist. Rocker arm 50 also forces the spray nozzle 40 to retract inwardly through opening 32 of the enclosure 10 during the spraying process. The spray pump 46 retracts back to its normal position via the action of spring 47.

Therefore, the fragrance holder 16 provides a container for storing a desired fragrance that may be concentrated and scented as desired. One end 15 of the fragrance holder 16 has a threaded male member 48 that receives the spray pump 46 via threaded sprayer member 44. As such the threaded sprayer member 44 can be conveniently removed to allow additional fragrance to be deposited inside the fragrance holder 16.

With reference to FIGS. 2 and 5, the flexing property of the mounting plate 18 is shown as a curvature along one of many possible contours. Grasps 84, 88 extend from the mounting plate 18 and act to secure the mounting plate 18 to the base 14 via slots 72, 74, 76,78. Tabs 56, 58, and 60 allow the base 14 to attach to the cover 12 of that forms the enclosure 11. Thus, the present invention provides a self-contained fragrance dispensing assembly that can be easily opened for refill purposes and reassembled for use.

FIG. 6 shows the bathroom fragrance dispenser 10 of the present invention mounted around the seat of a commode. The flexible mounting plate 18 has been flexed to allow the dispenser 10 to adapt to the contours of the commode. As stated above, the adhesive sheet 20, which is attached to the underside of the mounting plate 18 opposite the dispenser base 14, allows the dispenser 10 to be coupled to the curved commode surface. In this embodiment, commode users have quick and convenient access to the fragrance holder 16 whenever the need to deodorize a bathroom arises.

FIG. 6 also shows a wall mounted version of the fragrance dispenser 10 of the present invention. In this case, the base 14 as discussed earlier includes openings 95 and 97 adapted to receive fasteners (such as a screw, bracket, anchor or other similar device) for securing the dispenser 10 on a flat surface, such as on a bathroom wall or counter top. While the fragrance dispenser 10 is shown mounted on a commode and wall, it should be understood that use of the fragrance dispenser 10 of the invention is not limited to these two applications. For example, the fragrance dispenser 10 can be mounted on the tank of a commode, on a counter top or other suitable location.

Having described the present invention and illustrated its features and embodiments, one skilled in the art will appreciate its many advantages. For example, one advantage of the fragrance dispenser 10 is that it offers the user the convenience of not having to search for a deodorizer that is lost or misplaced since the dispenser 10 is designed to allow easy attachment near the source of odors.

Another advantage of the present invention is that it may be easily disassembled and fragrances of numerous scent varieties and of different odor intensities may be placed inside the fragrance holder 16 at any time. Overall, the fragrance holder 16 provides a cost effective refill mechanism for the user.

While the invention has been described with reference to illustrative embodiments, this description is not intended to be construed in a limiting sense. Various modifications and combinations of the illustrative embodiments as well as other embodiments of the invention will be apparent to persons skilled in the art upon reference to the description.

What is claimed is:

1. A fragrance dispenser comprising:

an enclosure comprising a base and a cover which can be attached to said base, said enclosure having an opening;

a fragrance holder within said enclosure;

a nozzle coupled to said fragrance holder and protruding through said opening;

a mounting plate coupled to said base for attaching the fragrance dispenser to a surface;

wherein a pressure applied to said enclosure causes a fragrance within said fragrance holder to dispense through said nozzle; and wherein said mounting plate is flexible and capable of assuming a plurality of contours.

2. A fragrance dispenser comprising:

an enclosure comprising a base and a cover which can be attached to said base, said enclosure having an opening;

a fragrance holder within said enclosure;

a nozzle coupled to said fragrance holder and protruding through said opening;

a mounting plate coupled to said base for attaching the fragrance dispenser to a surface;

wherein a pressure applied to said enclosure causes a fragrance within said fragrance holder to dispense through said nozzle;

wherein said base includes slots; and wherein said mounting plate further comprises grasps adapted to be insertable in said slots, each of said grasps including a plurality of fins that can secure said mounting plate to said base about said slots at a plurality of positions allowing said mounting plate to flex into a plurality of contours.

3. A fragrance dispenser comprising:

an enclosure comprising a base and a cover which can be attached to said base, said enclosure having an opening;

a fragrance holder within said enclosure;

a nozzle coupled to said fragrance holder and protruding through said opening;

a mounting plate coupled to said base for attaching the fragrance dispenser to a surface;

wherein a pressure applied to said enclosure causes a fragrance within said fragrance holder to dispense through said nozzle; and wherein said base includes a major surface with an opening therein and wherein said mounting plate further comprises a tab adapted to be insertable through said opening for securing said mounting plate to said base.

4. A bathroom fragrance dispenser comprising:

a cover having an opening at one end;

a base coupled to said cover to form an enclosure, said base including a major surface with slots formed therein;

a fragrance holder within said enclosure and having a nozzle protruding through said opening;

a flexible mounting plate comprising grasps adapted to be insertable in said slots of said base, each of said grasps including a plurality of fins that can secure said mounting plate to said base about said slots at a plurality of positions allowing said mounting plate to flex and assume the contour of a commode, tank, or other surface;

wherein a pressure applied to said cover causes a fragrance within said fragrance holder to dispense through said nozzle.

5. The bathroom fragrance dispenser according to claim 4 further comprising an adhesive sheet attached to said mounting plate for securing said dispenser to a surface.

6. The bathroom fragrance dispenser of claim 4 wherein said fragrance holder further comprises:

a spray pump coupled to said fragrance holder;

a sprayer head slidably engaged with said spray pump along a line substantially parallel to the length of said fragrance holder; and a tube coupled to said spray pump and adapted to be insertable in said fragrance holder;

wherein a pressure applied to sprayer head causes said spray pump to spray a fragrance from within said fragrance holder through said tube.

7. The bathroom fragrance dispenser of claim 6 further comprising:

a rocker arm within the space defined by said enclosure; and supports holding said rocker arm inside said base;

wherein said rocker arm is adapted to rotate in response to a pressure applied to said cover and compress said spray pump causing said spray pump to spray a fragrance contained in said fragrance holder through said nozzle.

8. The bathroom fragrance dispenser of claim 4 wherein said base includes an opening predisposed on said major surface and wherein said mounting plate further comprises a tab adapted to be insertable through said opening for securing said mounting plate to said base.

9. The bathroom fragrance dispenser of claim 4 wherein said base includes at least two openings for inserting a fastener, hook, nail or other similar device capable of securing said dispenser to a flat surface.

* * * * *